(12) United States Patent
Rapoport

(10) Patent No.: US 7,646,274 B2
(45) Date of Patent: Jan. 12, 2010

(54) APPARATUS AND METHOD FOR NON-INVASIVE MEASUREMENT OF CARDIAC OUTPUT

(76) Inventor: Uri Rapoport, Meshek 17, Moshav Ben-Shemen (IL) 73115

( * ) Notice: Subject to any disclaimer, the term of this patent is extended or adjusted under 35 U.S.C. 154(b) by 439 days.

(21) Appl. No.: 10/837,243

(22) Filed: Apr. 30, 2004

(65) Prior Publication Data

US 2005/0085712 A1    Apr. 21, 2005

(51) Int. Cl.
*H01F 1/00*    (2006.01)
(52) U.S. Cl. .................. 335/296; 600/410; 324/320; 324/318; 335/302
(58) Field of Classification Search ......... 335/296–306; 324/300–322; 600/410–435
See application file for complete search history.

(56) References Cited

U.S. PATENT DOCUMENTS 5,462,054 A * 10/1995 Rapoport et al. ............ 335/296
5,923,235 A *  7/1999 Van Oort ..................... 335/301

* cited by examiner

*Primary Examiner*—Brian Casler
*Assistant Examiner*—John F Ramirez
(74) *Attorney, Agent, or Firm*—Jerry A. Schulman

(57) ABSTRACT

A comparatively light and compact permanent magnet arrangement for an MRI apparatus has a pair of opposed permanent magnet arrays with a shimming system to adjust the uniformity and strength of a magnetic field in a central chamber of the apparatus. The MRI apparatus is used to examine the extremities of a patient to determine cardiovascular characteristics from an analysis of the blood flow through selected arteries in the extremity. The information collected can be used to calculate such characteristics as total cardiac output, blood flow, arterial wall thickness and elasticity and the presence of plaque.

15 Claims, 8 Drawing Sheets

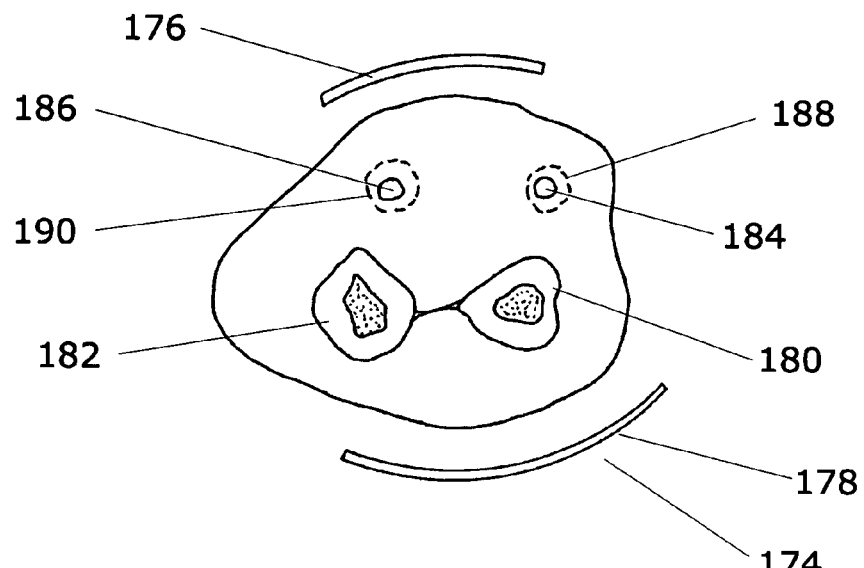
Fig. 8
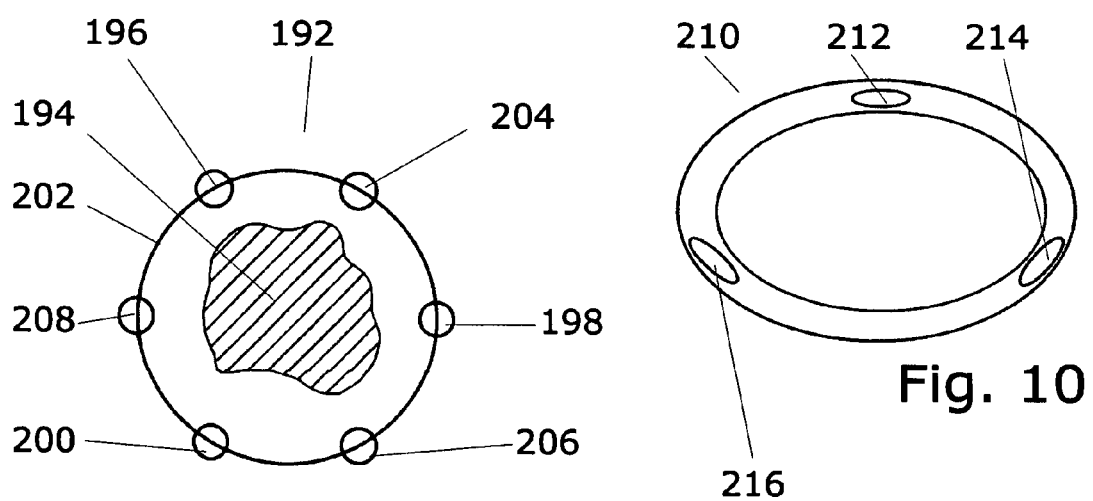
Fig. 9
Fig. 10

APPARATUS AND METHOD FOR NON-INVASIVE MEASUREMENT OF CARDIAC OUTPUT

BACKGROUND OF THE INVENTION

This invention relates generally to the measurement of cardiac output and, more particularly, to apparatus and methods for non-invasively measuring cardiac output and claims priority from application Ser. No. 60/467,015 of the same title, filed 1 May 2003.

Cardiac output is the volume of blood pumped by the heart during a given interval of time. Measuring cardiac output is a diagnostic technique used to evaluate cardiac function and detect the presence of cardiovascular disease or abnormality. Normally, cardiac output varies to meet the body's demand for oxygen and for nutrition. The left side of the heart receives oxygenated blood from the lungs and contracts, pumping the blood through arteries to all parts of the body. Blood flow is affected by such factors as the contractility of the left ventricle, the resistance against which the heart must pump and the volume of blood in the ventricle when pumping occurs.

Changes in cardiac output may indicate disease or may be evidence of an abnormality or change in a patient's cardiovascular system. Accordingly, measurement of cardiac output is a useful diagnostic tool and detection of changes in cardiac output may allow a physician to investigate a patient's condition more thoroughly and take measures to prevent serious or permanent damage.

Ideally, measurement of cardiac output should be quick, convenient, safe for the patient and should use equipment and techniques which are reliable, easy to operate and accurate.

There are a number of known techniques and devices for measuring cardiac output. One is the Fick method based upon work done by Adolph Fick in about 1870. As performed today, the Fick method involves injecting a measured amount of oxygen into an artery and then measuring the concentration of oxygen at a selected site downstream of the injection site. Typically, such a procedure involves the insertion of two catheters into a patient's body, one for the injection of the oxygen and the other for the collection of blood which is then analyzed and the oxygen content determined. While this technique produces satisfactorily accurate results, it does require surgically invasive procedures and the removal of an appreciable amount of blood which must then be analyzed, resulting in a measurement that is not a real time measurement. Whenever an invasive procedure is performed, it carries with it the attendant risk of possible infection.

In another technique for measuring cardiac output a dye is injected into the bloodstream and the dye concentration is measured at a point downstream of the injection site. Alternatively, a bolus of a chilled fluid indicator is injected and the temperature of blood withdrawn from a site downstream of the injection site is measured.

These and other cardiac output measurement techniques are well represented in the prior art.

The following references are representative of known invasive measurement techniques.

U.S. Pat. No. 5,797,395 (Martin) teaches and describes a continuous cardiac output derived from arterial pressure wave form using pattern recognition. Martin uses a fluid catheter installed in the bloodstream to measure the arterial pressure of a patient and to digitize the data collected by the sensors. The collected data is then compared to representative data stored in a database with representative wave forms corresponding to various levels of cardiac output.

U.S. Pat. No. 6,299,583 (Eggers) teaches and describes monitoring total circulating blood volume and cardiac output. Eggers et al uses a variation of the indicator dilution technique in which a test substance or analyte is injected into the body. As seen in FIG. 1 of Eggers et al, analyte is injected into the bloodstream by way of a catheter inserted into the subclavian vein leading to the heart. A catheter with a sensor is inserted into, for example, the radial artery in one of the patient's arms and is used to detect and measure the concentration of analyte.

U.S. Pat. No. 6,186,956 (McNamee) teaches and describes a method and system for continuously monitoring cardiac output without having to inject substances into the patient's body nor withdraw liquids from the body. McNamee does so by using a pressure transducer placed in a patient's mouth or a tracheal cannula in measuring the differential in pressure as the patient breathes in and out. The detection of this signal is then correlated to a table of known values from which cardiac output is deduced. McNamee references the use of MRI as an acceptable non-invasive measurement technique and also states that such techniques typically require large, expensive equipment and highly trained technicians to operate the equipment and interpret the results.

U.S. Pat. No. 6,322,518 (Young et al) teaches and describes a method and apparatus for measuring cardiac output which utilizes an esophageal probe inserted down the patient's throat to measure thoracic impedance variations which are then correlated to a measurement of cardiac output.

Even minimally invasive procedures require skilled technicians, risk infection and allergic responses, and cause apprehension and discomfort in the patient. The advantages of using non-invasive techniques for measuring cardiac output have been recognized in the prior art.

U.S. Pat. No. 6,306,098 (Orr et al) teaches and describes apparatus and method for non-invasively measuring cardiac output. Orr et al use a modification of the Fick approach, measuring the difference in carbon dioxide concentration between the air inhaled and exhaled by a patient through a breathing tube rather than measuring concentration of oxygen at disparate points in the patient's bloodstream. A computer program is used to calculate cardiac output based upon the differential in carbon dioxide concentration.

U.S. Pat. No. 5,458,126 (Cline et al) teaches and describes a cardiac functional analysis system employing gradient image segmentation. Cline et al describe the use of techniques such as computed axial tomography (CAT) and MRI to create a four-dimensional data set to create images of selected portions of the cardiovascular system.

Cline et al are representative of the use of complex, expensive and quite large equipment to carry out these measurements.

U.S. Pat. No. 5,417,214 (Roberts et al) teaches and describes quantitative blood flow measurement using steady-state transport induced adiabatic fast passage. Again, Roberts et al is representative of the complexity presently experienced in the use of MRI to carry out cardiovascular measurements and evaluation. In particular, at column 5, lines 26 et seq. Roberts et al describe the necessity for precise techniques for gathering the data used in the analysis.

U.S. Pat. No. 6,348,038 (Band et al) teaches and describes method and apparatus for the measurement of cardiac output using the wave form created by the measurement of arterial blood pressure in a patient. The collected data is used to determine nominal stroke volume and using this determination to obtain a nominal value for the patient's cardiac output.

U.S. Pat. No. 5,360,005 (Wilk) teaches and describes a medical diagnosis device for sensing cardiac activity and blood flow. Wilk uses an acousto-electric transducer as a type of stethoscope to convert heart sounds into electric impulses and then uses a microprocessor to analyze these impulses and correlate them to cardiovascular activity.

U.S. Pat. No. 4,509,526 (Barnes et al) teaches and describes method and system for non-invasive ultrasound Doppler cardiac output measurement. Barnes et al teach the positioning of a transducer at separate locations on a patient's body to determine ultrasonically the cross-sectional area of a patient's ascending aorta and to determine the systolic velocity profile of blood flow through the aorta, enabling the calculation of cardiac output. To practice the technique described in Barnes et al the transducer must be accurately positioned by a technician at two separate sites in order to generate the data required to make the calculations necessary to determine cardiac output.

U.S. Pat. No. 5,178,151 (Sackner) teaches and describes a system for non-invasive detection of changes of cardiac volumes and aortic pulses. Sackner et al use transducers positioned on the patient's body to send and receive signals which include a wave form characteristic of the ventricular volume and then continuously monitors to detect changes in the wave form.

U.S. Pat. No. 5,443,073 (Wang et al) teaches and describes a system and method of impedance cardiography monitoring using body-mounted electrodes to collect EKG signals which are then mathematically processed to predict stroke volume.

U.S. Pat. No. 5,423,326 (Wang et al) teaches and describes apparatus and method for measuring cardiac output in which transducers are attached to a patient's body and the signals generated and collected by these transducers are transformed and analyzed to correlate these signals to cardiac output.

U.S. Pat. No. 5,309,917 (Wang et al) teaches and describes a system and method of impedance cardiography and heartbeat determination using a combination of thoracic impedance and electrocardiogram signals with the data represented by these signals processed to determine such characteristics as stroke volume and cardiac output.

U.S. Pat. No. 5,685,316 (Schookin et al) teaches and describes a non-invasive monitoring of hemodynamic parameters using impedance cardiography. Bioimpedance electrodes are used to collect data across a patient's thoracic region and the data so collected are analyzed and correlated to heart stroke volume from which cardiac output is calculated.

Although diagnostically useful, the foregoing art references demonstrate serious drawbacks ranging from the size, complexity and expense of the equipment used to obtain information to the requirement that the instruments used to collect the data. As an example, thoracic impedance systems use EKG leads which must be accurately positioned on and attached to a patient's body in order to effect the collection of data that is later translated into values for cardiac output.

In a text entitled "Magnetic Resonance of the Heart and Great Vessels", edited by J. Bogaert, A. J. Duerinckx and F. E. Rademakers (Springer-Verlag, Berlin 2000) the principles of MRI as applied to cardiology are set forth in Chapter 1, entitled "Techniques for Cardiac MRI", written by H. Bosmans. MRI examination begins with placing the patient within a strong, static magnetic field which aligns the spins of the protons contained in body tissues and fluids. Thereafter a radio frequency (RF) pulse is used to excite the protons and disturb the alignment of the protons with the magnetic field. A coil or detector is used to capture the signal produced by this change in alignment and return to the original alignment. The signal is influenced by two "relaxation times", T1 and T2, generally described as measuring the times it takes the longitudinal and transverse components of the "excited" protons to return to the aligned state. The resulting signals are characteristic of the type of tissue being examined and are processed to create an image of the tissues being studied.

The use of MRI in cardiac examination is also described in the March 2001 issue of *Medica Mundi* in an article reprinted from "Heart Care" written by E. Nagel and E. Fleck, beginning at page 23. At page 29 of the article, the use of MRI to determine blood flow velocities is discussed and the need for more accuracy in the equipment used is identified.

MRI technology is used to diagnose coronary disease by examining the flow of blood through blood vessels located in the arms. In one such proposed technique, the flow of blood is occluded with an inflatable cuff and MRI is used to measure the dilation of the blood vessels and the shear stress generated by the force of blood flow against the endothelial cells. Under normal circumstances, the endothelial cells will produce the chemical nitric oxide to cause the coronary arteries to widen thus increasing blood flow to the heart and other muscles during times of stress. In a patient with coronary artery disease this effect my be greatly attenuated.

Accordingly, the need exists for apparatus and methods to determine cardiac output which are wholly non-invasive, require no leads or other data collection devices to be attached to the patient, utilize recognized accurate diagnostic techniques such as MRI and which may be used in obtaining quick and accurate measurement of cardiac output without requiring significantly complex placement or measurement techniques.

A further object of the present invention is to provide an MRI unit which is relatively small and inexpensive yet which provide the precision and resolution necessary to make accurate measurements of cardiac output.

A further object is to make such equipment easy to operate without the use of time-consuming or complex diagnostic techniques.

A further object is to provide methods for the use of such equipment to make the required measurements carrying out such measurements on a patient's extremities rather than the thoracic cavity or the heart itself.

A further object is to avoid the use of drugs, analytes, dyes, tracers and other foreign substances.

The present invention is concerned with apparatus and methods to carry out the analysis of blood flow, preferably in the radial and ulnar arteries. The apparatus consists of an MRI unit significantly smaller in size than the fill-body MRI units presently used to conduct cardiovascular examination. A pair of opposed magnet assemblies joined by a magnetically conductive yoke defines an air gap between the assemblies. When a patient's arm is placed within the air gap the unit is used to carry out MRI analysis of the blood vessels in the arm. Internal and peripheral shimming mechanisms allow the uniformity of the magnetic field to be adjusted, and the configuration of the magnets creates a magnetic field of about 1.0 tesla. A preferred configuration of the apparatus will be approximately 60 cm. by 60 cm. in cross-sectional size and will weigh about 250 kg.

BRIEF DESCRIPTION OF THE DRAWINGS

These and further objects of the present invention will become more apparent upon consideration of the accompanying drawings wherein:

FIG. 8 is a cross-section of a patient's arm illustrating measurement of the radial and ulnar arteries;

FIG. 9 is a schematic view of an RF coil array used with the present invention;

FIG. 10 is a cross-sectional view of a sleeve worn by a user of the present invention;

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

Figure 1:
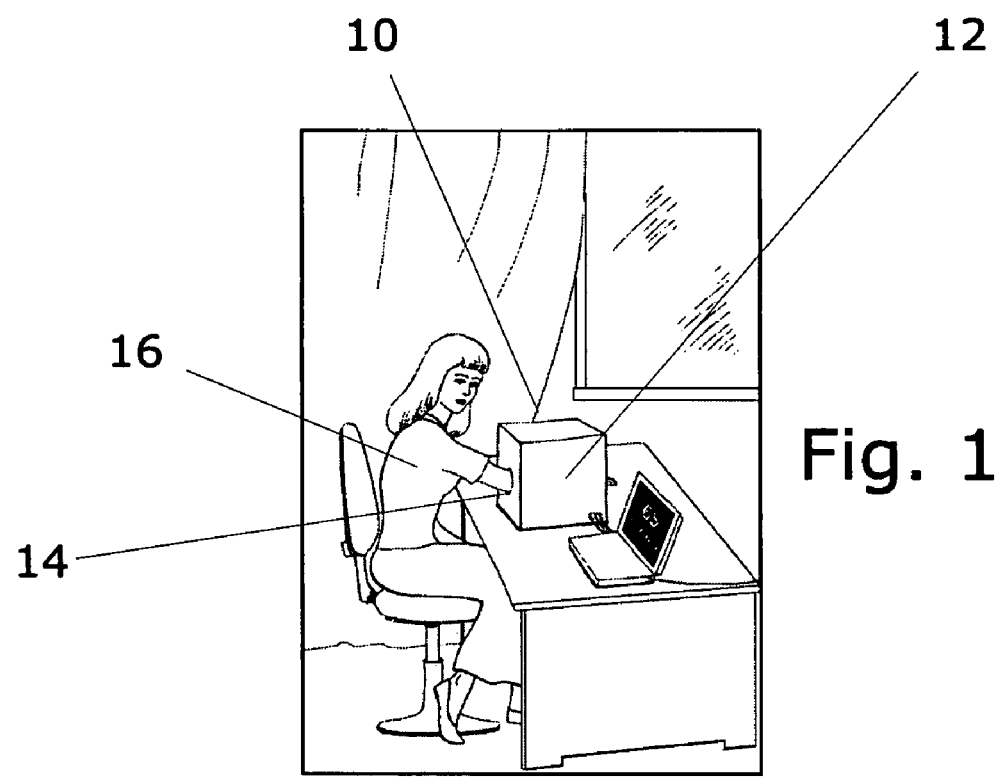
FIG. 1 is an illustration showing use of apparatus embodying the present invention to examine the arm of a supine patient.
Figure 2:
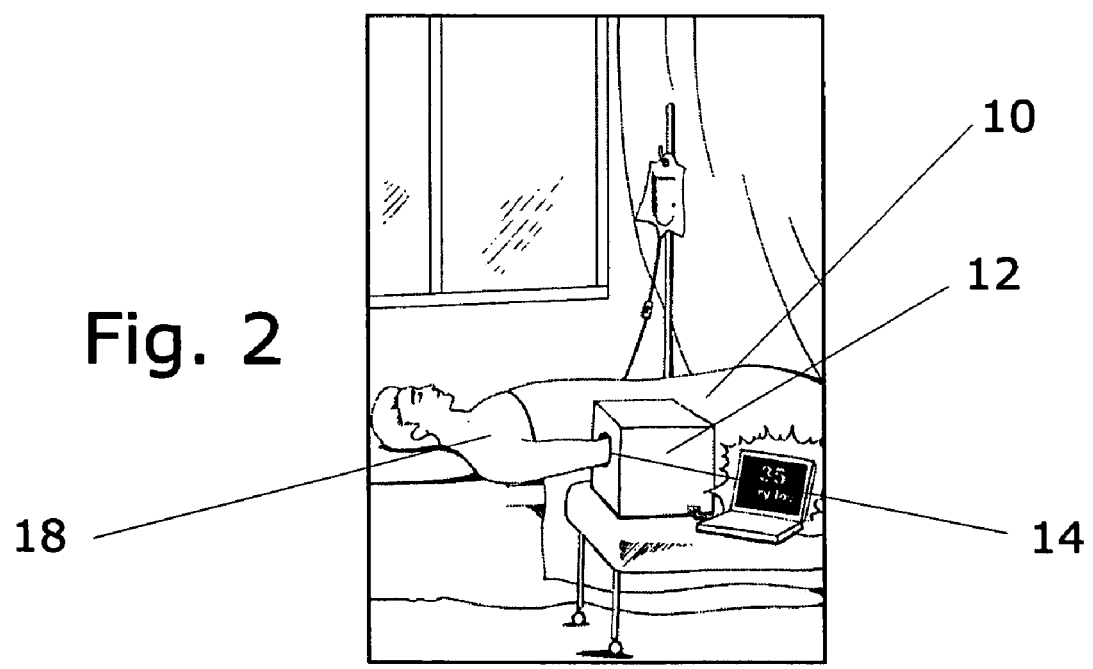
FIG. 2 is an illustration showing use of the present invention to examine the arm of a patient seated at a desk.

Referring now to FIG. 1, the numeral 10 indicates generally a diagnostic apparatus consisting generally of a cabinet 12 within which a permanent magnet assembly is disposed. Access to the cabinet is via a port 14 through which a patient 16 inserts his or her arm to place the arm within a magnetic field created by the magnet assembly. As seen in FIG. 2, the same apparatus can be used for a patient 18 when in the supine position. Apparatus 10 is relatively lightweight, compact in size and capable of providing real-time data.

Figure 3:
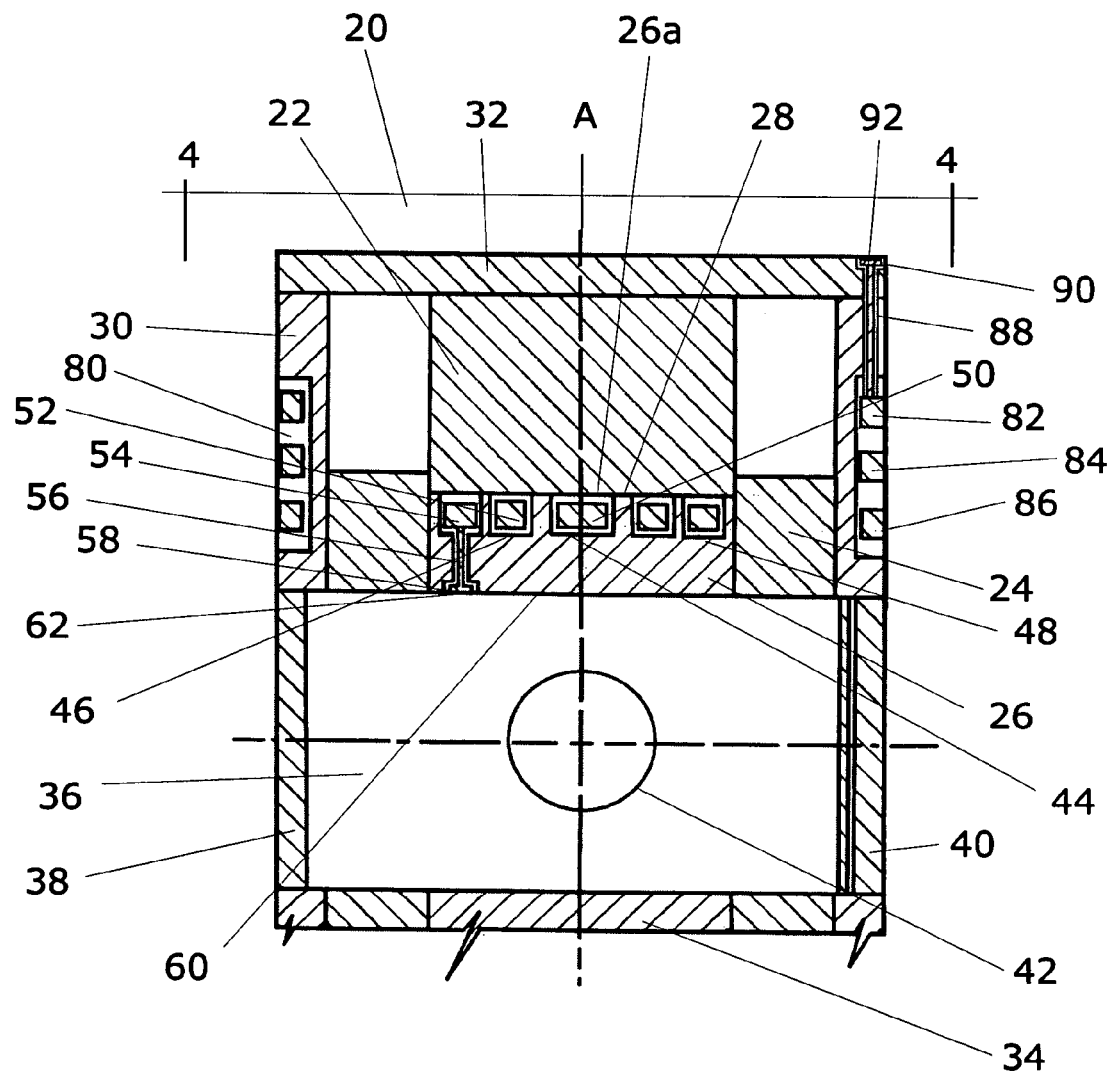
FIG. 3 is a partial sectional view of a first permanent magnet arrangement designed for use with the present invention.

Referring now to FIG. 3, the numeral 20 indicates generally a sectional view of a first permanent magnet assembly designed for use in diagnostic apparatus 10.

Assembly 20 consists of a steel main magnet 22 formed as a solid right circular cylindrical section having a vertical axis A. A circular toroidal side magnet 24 is positioned coaxially with main magnet 22 about axis A and in this preferred embodiment has a rectangular or square cross-section. A steel pole piece 26, formed as a solid right cylindrical section equal in diameter to main magnet 22 is positioned in face-to-face contact with main magnet 22 at main magnet face 28. This entire assembly is positioned within a hollow steel sleeve 30 which is closed off by a steel end cap 32.

In a preferred embodiment of the present invention, first permanent magnet assembly 20 is placed in face-to-face relationship with an identical permanent magnet assembly 34 having identical components to and spaced apart from first magnet assembly 20 to form an air gap 36 therebetween. Sleeve 30 extends to enclose magnet assemblies 20,34 and air gap 36. A pair of removable side walls 38,40 allow access to air gap 36 when removed from sleeve 30.

Permanent magnet assemblies 20, 34 are opposite in polarity to create a magnetic flux field across air gap 36. A centrally located segment of air gap 36 is identified in FIG. 3 as diagnostic zone 42 across which the magnetic flux is at its most powerful and its most uniform.

Magnet assembly 20 includes means for adjusting the flux field across zone 42.

In a first embodiment of magnet assembly 20, pole piece 26 has a first centrally located cylindrical cavity 44 formed in interior face 26a. A second, circular cavity 46 is formed coaxial with cavity 44 and a third circular pole piece cavity 48 is similarly formed, coaxial with cavities 44 and 46.

Disposed within cavity 44 is a first cylindrical steel shim 50. Disposed within second circular cavity 46 is a toroidal steel shim 52 and disposed within third circular cavity 48 is a second toroidal steel shim 54.

Each shim 50, 52, 54 is adjustable along an axis parallel to axis A of permanent magnet assembly 20. A preferred embodiment of the adjusting mechanisms for shim 54 is shown in FIG. 3. A shaft 56 is bored through terminating in a countersink 58 larger in diameter than that of shaft 56 and extending to face 60 of pole piece 26. A threaded fastener, such as a bolt 62, is journalled to shim 54 and shim 54 may be adjusted with respect to face 60 by turning bolt 62 to move shim 54 toward or away from face 60.

At least three such bolts are attached to shim 54 and are placed equidistantly about the circumference of shim 54.

Figure 4:
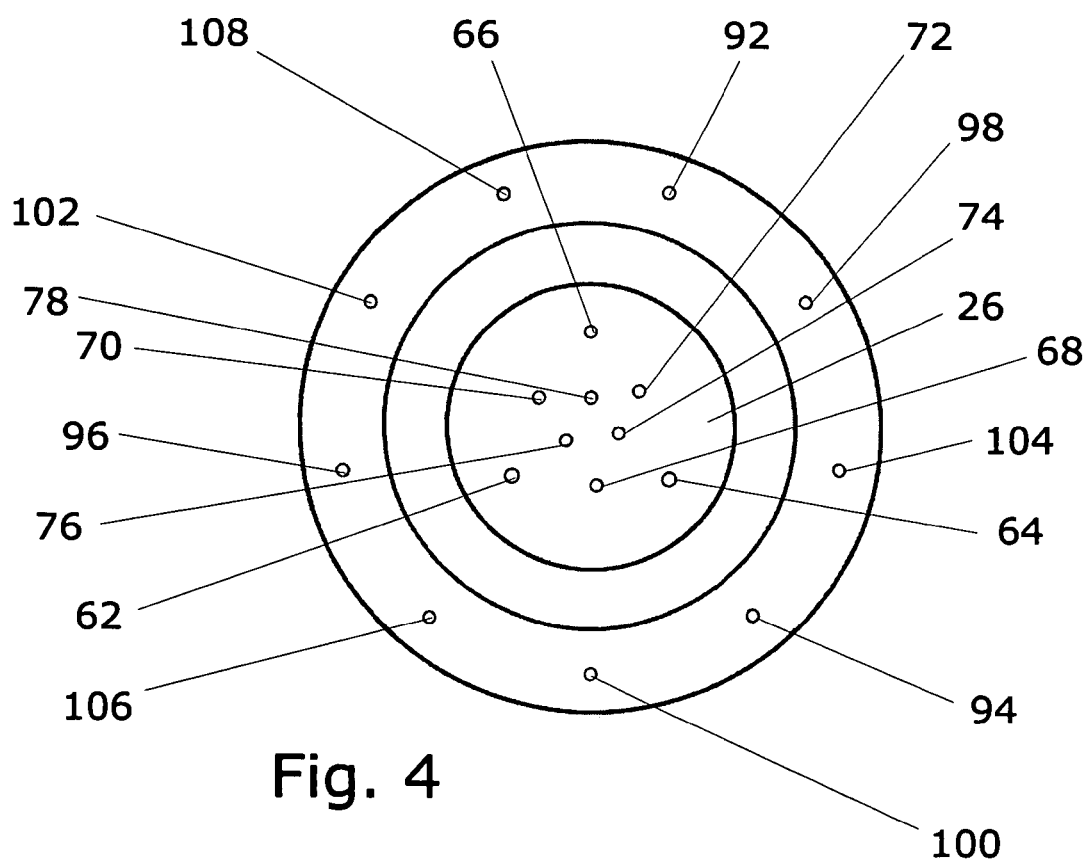
FIG. 4 is a view along 4-4 of FIG. 3.

FIG. 4 is a view taken along 4-4 of FIG. 3 and illustrates the positioning of the shafts and adjusting bolts for each of the shims. In FIG. 4, bolts 62, 64 and 66 are attached to and serve to adjust shim 54. In like fashion, bolts 68, 70 and 72 are attached to and work to adjust first shim 52. Bolts 74, 76 and 78 are journalled to and serve to adjust cylindrical shim 50.

In a preferred embodiment of magnet assembly 20, a second set of toroidal steel shims are provided for the purpose of strengthening and adjusting the linearity of the magnetic flux field across air gap 36.

As seen in FIG. 3, steel sleeve 30 has a circumferentially extending channel 80, a concentric set of toroidal steel shims 82, 84, 86 are positioned in channel 80 and are supported and adjusted by a series of adjusting bolts such as those described in connection with shims 50, 52 and 54. As seen in FIG. 3, a bore 88 is formed extending through end cap 32 and having a countersink 90 formed at the end thereof. An adjusting bolt 92 is threadedly journalled to sleeve shim 82. A minimum of three such adjusting bolts are provided for each said shim and, as seen in FIG. 4, identical adjusting bolts are provided for sleeve shims 84 and 86. FIG. 4 shows, in section, bolts disposed in bores such as bore 88, with bolts 92, 94 and 96 attached to shim 84, bolts 98, 100 and 102 attached to shim 84 and bolts 104, 106, and 108 attached to shim 86.

Figure 5:
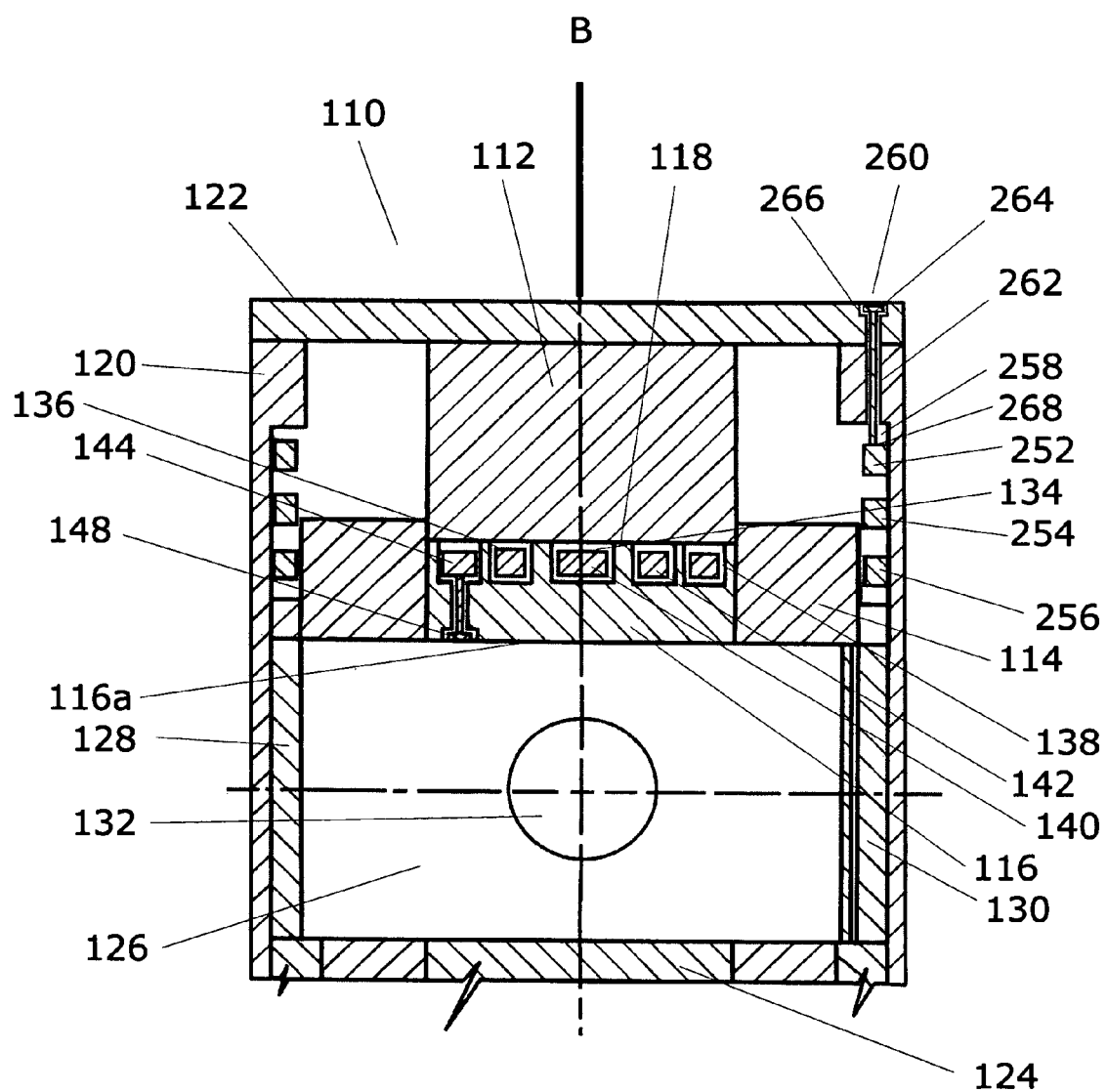
FIG. 5 is a partial sectional view of a second permanent magnet arrangement designed for use with the present invention.

Referring now to FIG. 5 the numeral 110 indicates generally a sectional view of a second permanent magnet assembly designed for use in diagnostic apparatus 10.

Magnet assembly 110 consist of a steel main magnet 112, formed as a solid right circular section having an axis B. A circular toroidal side magnet 114 is positioned coaxially with main magnet 112 about axis B. In the embodiment shown herein, side magnet 114 has a square cross section although cross sections of varying shapes may be selected. A steel pole piece 116, formed as a right solid cylindrical section equal in diameter to main magnet 112 is positioned in face-to-face with main magnet 112 and main magnet face 118. The entire assembly is positioned within a right cylindrical steel sleeve 120 which is closed off by a cylindrical steel end cap 122.

As with first magnet assembly 20, and consistent with a preferred embodiment of the present invention, second permanent magnet assembly 110 is placed within sleeve 120 in face-to-face relationship with an identical, mirror image permanent magnet assembly 124 having identical components and construction and spaced apart from second magnet assembly 110 to form an air gap 126 therebetween. Steel sleeve 30 extends to enclose magnet assemblies 110, 124 and air gap 126.

A pair of removable side walls 128, 130 allow access to air gap 126 when removed from sleeve 120. Permanent magnet assemblies 110, 124 are opposite in polarity to create a magnetic flux field across air gap 126. A centrally located segment of air gap 126 is identified in FIG. 5 as a diagnostic zone 132 across which the magnetic flux is at its most powerful and uniform. For purposes of illustration, face 118 of main magnet 112 has a north polarity while the corresponding face of the main magnet in magnet assembly 124 has a south polarity. As with magnet assembly 20, magnet assembly 110 includes means for adjusting the linearity of the flux field across air gap 126. In this second permanent magnet assembly embodiment, 110, exterior face 116a of pole piece 116 has a first centrally located cylindrical cavity 134 formed therein. A second, circular cavity 136 is formed coaxial with cavity 134 and a third circular pole piece cavity 138 is similarly formed, coaxial with cavities 134 and 136.

As seen in FIG. 5, a first steel shim 140 is disposed within cavity 44. Shim 140 is formed as a solid right cylindrical section or disk. Disposed within second circular cavity 136 is second steel shim 142 formed as a toroid and disposed with a third circular cavity 138 is a third steel shim 144 also formed as a toroid. In the preferred embodiment shown in FIG. 5, shims 142 and 144 are formed with square or rectangular cross-sectional shapes although other shapes may be selected as found desirable or necessary.

Figure 6:
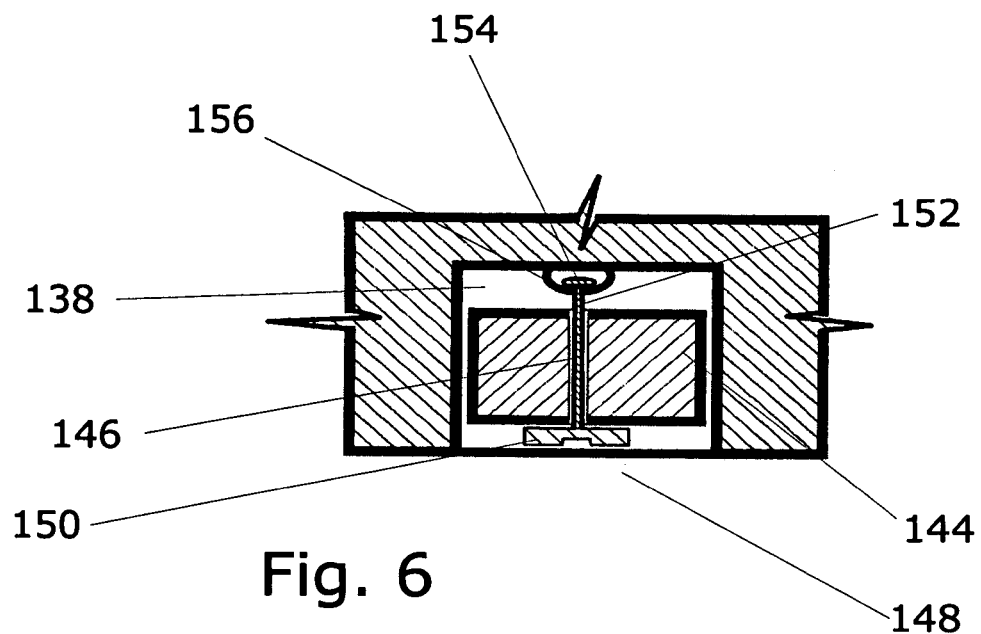
FIG. 6 is an enlarged sectional view of an adjustable pole piece shim shown in FIG. 5.

Each shim 140, 142 and 144 is adjustable along an axis parallel to axis B of permanent magnet assembly 110. A preferred embodiment of the adjusting mechanism for shim 144 is shown in FIG. 6. Shim 144 has a series of tapped or threaded apertures 146 formed parallel to axis B. In a preferred embodiment, apertures 146 are formed midway to the inner and outer diameters of shim 144 and at regularly spaced intervals. For example, three such apertures may be formed displaced one from the other by an angle of 120 degrees. An adjusting screw 148 has a head 150 and a shaft 152, with shaft 152 sized and threaded to engage tapped aperture 146. End 154 of shaft 152 is rotatably journalled to and supported by a support 156, allowing screw 148 to rotate in either a clockwise or counterclockwise direction. As screw 148 is rotated, shim 144 travels along shaft 152 as shaft 152 threads along tapped aperture 146.

Referring again to FIG. 5, a series of sleeve shims 252, 254 and 256 are shown concentrically disposed in a circumferentially extending channel 258 formed in sleeve 120. Shims 252, 254 and 256 are axially adjustable in the same manner as sleeve shims 82, 84 and 86 shown in FIG. 3. A representative threaded adjusting bolt 260 passes through a threaded bore 262 with bolt head 264 seated in countersink 266. Bolt end 268 is journalled to sleeve shim 252 in the same manner as shown in FIG. 6 and shim 252 is adjusted axially by threading bolt 260 along bore 262. Preferably, at least three such adjusting bolts are provided for each sleeve shim, spaced at regular intervals.

Figure 7:
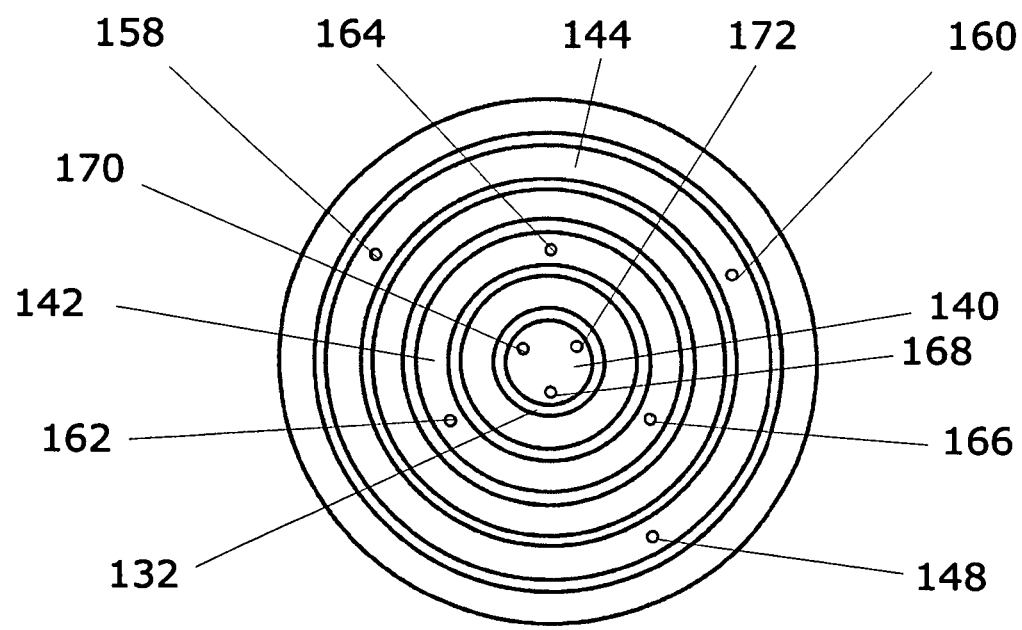
FIG. 7 is a view along 7-7 of FIG. 5.

Referring to FIG. 7, shim 144 is shown in cavity 138 and supported by adjusting screws 148, 158 and 160. Similarly, shim 142 is shown in cavity 134 and supported by adjusting screws 162, 164 and 166. Central disk shaped shim 140 is shown in cavity 132 and is supported by adjusting screws 168, 170 and 172.

When assembled, the pole piece shims and annular shims described above are adjusted to produce a magnetic field across air gap 36 and air gap 126 with a high degree of uniformity in field strength and field direction.

Apparatus 10 is used to practice non-invasive methods of assessing total cardiac output, relative cardiac output, arterial wall thickness and elasticity and flow mediated dilation. Measurement of these functions is carried out non-invasively on a real-time basis and in a setting which is convenient and comfortable for the patient. These measurements are used for initial examinations and to track changes in the circulatory system before and after a given treatment. Use of apparatus 10 in carrying out MRI examinations is not subject to the variations and results produced using such techniques as ultrasound where personnel must be highly trained to position accurately the probe used during examinations.

In a preferred embodiment of the present invention, apparatus 10 is used to perform an MRI examination of the radial and ulnar arteries in a patient's arm.

Referring now to FIG. 8, the numeral 174 identifies the arm of a patient shown in a schematic-type cross-section. For the purposes of illustrating the present invention, reference will be made to the permanent magnet arrangement shown in FIG. 3. Arm 174 is placed within apparatus 10 as shown in FIGS. 1 or 2 with arm 174 extending through air gap 36 and positioned within diagnostic zone 42. An RF coil 176 is positioned above arm 174 and a gradient or pickup coil 178 is positioned beneath arm 174 to receive the signal created when RF coil 176 is pulsed.

As seen schematically in FIG. 8, the radial and ulnar bones 180, 182 are shown, as are the radial and ulnar arteries 184, 186. As the heart beats, the blood pressure within the body's arterial blood vessels varies from a maximum (systolic) and minimum (diastolic) value. The systolic blood pressure represents pressure within the blood vessel during a heartbeat while the diastolic pressure is that measured when the heart is at rest between beats. Arteries 184, 186 are shown during the diastolic portion of the heartbeat cycle. When the heart beats, arteries such as 184, 186 expand as shown at 188, 190.

The apparatus and methods of the present invention measure and record the changes in size of arteries 184, 186 with the heartbeat and between heartbeats. In this fashion, the cross-sectional area of arteries 184, 186 can be determined. It is also known to determine the rate of flow of blood using commonly applicable MRI techniques and the combination of the determination of artery cross-sectional area and rate of flow allows calculation of the portion of the total cardiac output passing through the representative arteries during a heartbeat.

This information can be used to establish a baseline cardiac output for a patient with any deviation in output over time operating as an indicator that the patient's cardiac condition has changed. Cardiac output can also be calculated by using known values of the percentage of cardiac output normally passing through the radial and ulnar arteries and using this ratio to estimate total cardiac output. For the purposes of this description, total cardiac output is defined as the volume of blood pumped from the heart with each beat, approximately 12% of which moves through the brachial arteries of each arm with each beat and the detected blood flow volume can be compared to tables of known blood flow ratios for patients of different ages, weights and other variables.

MRI allows a cross-section to be taken that includes both arteries 184, 186 simultaneously. In order to create a high resolution image, it may be necessary to reposition the arm within the magnetic field prior to pulsing the RF electrodes. An alternative to physical repositioning is the use of an array of electrodes and a computer program to adjust the pulsing of the electrodes to produce improved images.

For purposes of accuracy, pick up coil 178 should be positioned as close as possible to the arteries being measured. Use of the relatively small diagnostic area 42 makes this possible and readings can be taken with the patient's arm extending into apparatus 10 with the palm either facing in the upward or downward position or rotated to produce an optimum image of the arteries.

Referring now to FIG. 9, the numeral 192 identifies generally an array of RF coils positioned around a patient's arm 194. RF coils such as those used as electrodes in MRI diagnostic equipment can be used as pulsing or receiving coils or can function as both pulsing and receiving coils. For a single coil to both pulse and receive, an rf signal is pulsed through the coil. This transmission is gated and after it has ceased the coil goes through a period of quiescent or "dead" time where no signal is being sent nor received. Thereafter, the coil is activated to receive the data produced by its own pulsed signal. The data signal is also gated to create a second period of dead time, after which the coil may then again be pulsed to transmit another signal.

As seen in FIG. 9, an array of RF coils 196, 198, 200 are positioned equidistantly about the circumference of array perimeter 202. It is possible to pulse these coils in sequence to create a "virtual coila" effectively positioned at selected points about the periphery of perimeter 202. It is also possible to mechanically rotate perimeter 202 to bring coils 196, 198, 200 into a different physical location with respect to arm 194. By performing actual or virtual rotation of the positions of coils 196, 198, 200 and selectively using each coil selectively to pulse energy, receive energy or both it is possible to adjust device 10 to produce the clearest possible image of arm 194.

To increase the sensitivity and adjustability of array 192, additional RF coils can be added to the array such as coils 204, 206, and 208 and to control the pulsing and collection capabilities of each coil by computer in order to adjust the received image.

Referring now to FIG. 10, the numeral 210 identifies a cross-sectional view of a tubular sleeve within which RF coils 212, 214 and 216 are disposed. Sleeve 210 can be formed of fabric and is intended to be slipped over the patient's arm or other appendage and to thereafter be placed within device 10. Sleeve 10 allows coils 212, 214, 216 to be placed as close to the area of examination as possible and to provide a uniform dispersion of signal transmission and collection independent of the placement of coils within device 10 itself.

As described in connection with array 192, sleeve 210 can include any selected number of coils and the arrangement shown in FIG. 10 is by way of example only.

Sleeve 210 can be formed as a permanent, flexible and expandable cuff or can be formed as a disposable unit which can be discarded after use. Sleeve 210 can be provided in a range of sizes to accommodate extremities of varying proportions, can be written upon to record patient information, and can contain various numbers and configurations of coils and coil leads that can selectively be connected to provide energy to selected coils.

Figure 11:
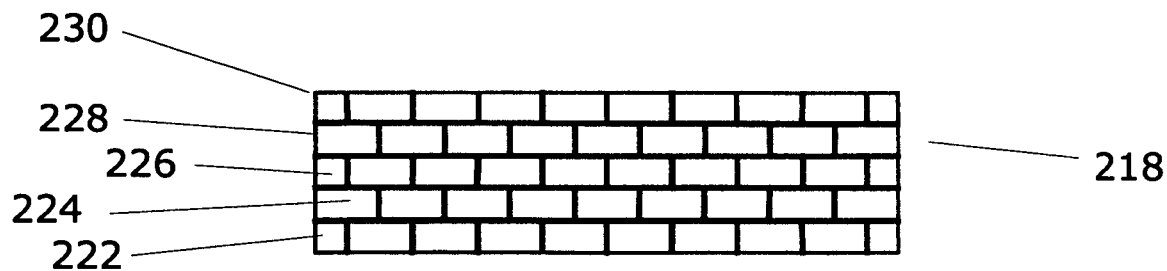
FIG. 11 is a lateral view of a second embodiment of the pole piece of FIG. 1.

Referring now to FIG. 11, an alternative construction for pole pieces such as pole piece 60 is shown. FIG. 11 is a cross-sectional view of a pole piece 218 constructed as a series of laminae 220, 224, 226, 228 and 230 glued together in a solid array by non-conductive epoxy glue or other well-known permanent adhesives.

Figure 12:
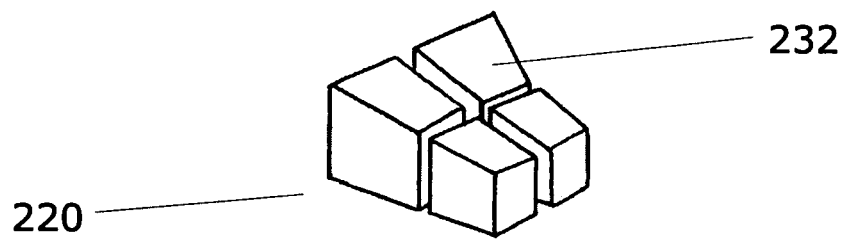
FIG. 12 is a plan view of the cubic elements making up the pole piece of FIG. 11.

As seen in FIG. 12, a section of laminae 220 is shown in partial perspective. Each laminae is formed of a series of cubes 232 preferably extruded from ferromagnetic material and glued together with the adhesives described above. In a preferred embodiment of the invention, each cube is approximately 10 mm by 10 mm by 10 mm. When cubes 232 have been solidly glued into a planar array, each such array is stacked and glued to corresponding arrays to produce the structure shown in FIG. 11. The completed array may then be machined to the shape desired to use the completed array as a pole piece.

Figure 13:
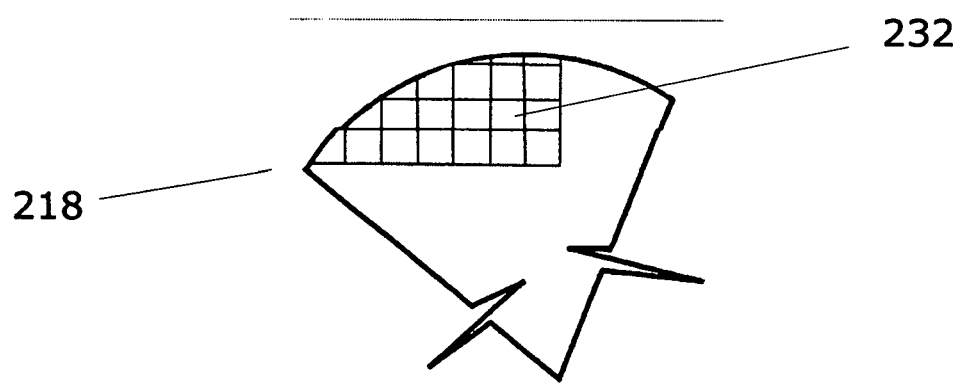
FIG. 13 is a partial view of a pole piece segment.

Use of cubic elements are believed to limit the eddy currents created within the ferromagnetic pole piece when the RF coils are pulsed. Referring now to FIG. 13, a top plan view of a segment of pole piece 218 is shown illustrating the appearances of cubes 232 when cemented into the array and shaped to be used as a pole piece. In assembling a laminated pole piece such as 218, cubes 232 are arranged such that the interfaces of adjacent cubes are offset from the interfaces of the cubes in the layers immediately above and below thereby adding strength to the array.

Figure 14:
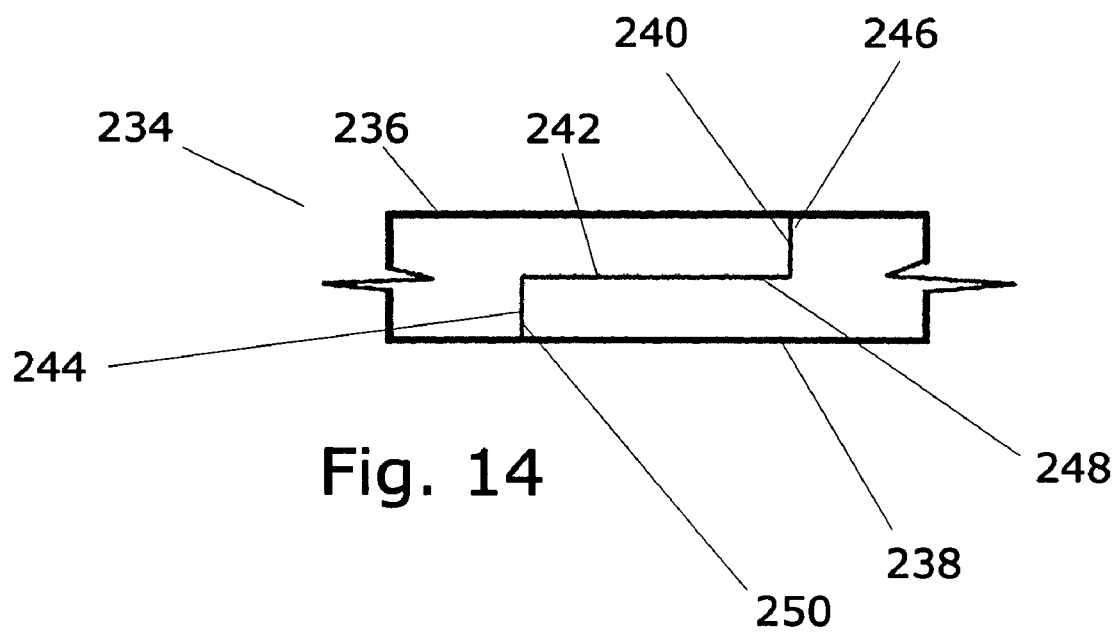
FIG. 14 is a partial lateral view of a second embodiment of the shim rings of FIG. 1.

Referring now to FIG. 14, the numeral 234 identifies a segment of an alternative construction of the torroidal shim rings such as 54 of FIG. 3. The embodiment of FIG. 14 shows shim 234 assembled from overlapping segments 236, 238 with segment 236 having an upper edge 240 and intermediate land 242 and a lower edge 244 while segment 238 has an upper edge 246 an intermediate land 248 and a lower edge 250. When assembled, edges 240, 246 abut as do lands 242, 248 and lower edges 244, 250. At each of these abutments, an epoxy or other suitable adhesive is used to permanently attach the segments together.

It is also contemplated that the torroidal and disk-shaped shims described earlier can also be constructed from laminae in the manner shown in FIGS. 11, 12, and 13. In such constructions, it is contemplated that cubes 232, when used in shim constructions, can be extruded from ferromagnetic metals, non-ferromagnetic metals, non-metallic substances or magnetic material.

While not herein specifically shown, it is acknowledged that the use of electromagnetic gradient coils as shims to adjust the linearity and shape of the magnetic field of a permanent magnet array is well known and can be included in the arrangements described herein. Such shim coils can also be used as gradient coils by pulsing the coils to intentionally distort the field of view to aid in distinguishing between tissues of different types. Preferably, separate shim and gradient coils are used to keep voltage to the shim coils constant.

The disclosed methods and apparatus offer advantages over prior known MRI diagnostic methods in that a relatively small permanent magnet arrangement is used to produce a high strength uniform and high resolution magnetic field across a very small part of the body. This is a much different approach than that described in the Nagel and Fleck article referenced above in which a patient is "positioned within the bore of a cylindrical superconducting magnet." The strength of the magnetic field produced by the present invention is estimated in excess of 1.0 tesla and the relatively small size of the body portion being sampled creates an image with a higher signal-to-noise ratio than can be achieved when the entire body is placed within a magnetic field. The resulting high resolution images allow the changes in size of the arteries to be accurately determined.

When performing MRI diagnostic procedures, care must be taken to avoid damage to nerves caused by too high a field gradient across the area of the body being examined. For the purposes of this description, the field gradient is described as the strength of the magnetic field divided by the area of the field of view in question. Using the greatly reduced field of view made possible by the present invention, allows for higher gradients to be safely used when examining patients. This results in higher resolution images and more accurate diagnostic information.

Total cardiac output can be estimated by relating the radial and ulnar arteries and comparing these measurements to known values of percentages of cardiac output measured through such arteries.

Use of the present invention thus allows cardiac functions to be examined in a strong, small magnetic field with a relatively high field gradient. This will also result in the capability of using rapid pulses to produce accurate images showing the changes in size of the arteries in question.

The apparatus described herein uses less energy and is less expensive to build than the presently known full body type MRI diagnostic units.

In evaluating cardiac function, the RF pulses may be timed to commence with the heartbeat and can be used to track changes in the heartbeat. Alternatively, use of the present invention may be used without using the heartbeat as a trigger or marker with the apparatus being operated through a sufficient number of cycles to guarantee that an entire cycle has been captured and accurately characterized.

Use of MRI to create images of arteries 186, 188 is superior to the use of ultrasound because MRI produces a cross-sectional view which allows the system to track the changes in size and configuration of arteries 186, 188. Ultrasound, on the other hand will provide only a lateral view and even though this lateral view can show changes in the apparent diameter of the arteries, it does not provide an accurate view of the actual cross-sectional configuration of the artery. Where an artery is, for example, not perfectly round or in some way impeded, the cross-section will be less than circular. However, MRI will enable the operator to determine the exact shape and, therefore, area of the cross-section and to calculate the blood flow therethrough.

Measurement of FMD using the radial and ulnar arteries has been shown to have a 95% correlation with the same measurements when measured at the coronary arteries. Measuring FMD, or endothelial dysfunction, correlates with well-known risk factors used to assess the health of the patient's cardiovascular system Using a multi-spectral or multi-contrast technique allows the technician to accurately determine the presence and thickness of any plaque layers in the artery, another indicator of general cardiovascular health.

The invention claimed is:

1. Apparatus for use in performing MRI analysis of living tissue, said apparatus comprising:
    a cylindrical housing formed from magnetically conductive material,
    said housing having a housing wall defining a space therewithin and having first and second open ends;
    a first permanent magnet arrangement comprising a first main magnet formed as a right, cylindrical solid having a central axis, an outer wall and first and second opposed faces perpendicular to said main magnet axis;
    a pole piece formed from ferromagnetic material,
    said pole piece having a central axis and first and second opposed pole piece faces perpendicular to said pole piece axis,
    the first of said pole piece faces being positioned at and coextensive with said first main magnet face;
    a side magnet,
    said side magnet having an inner opening sized and shaped to match the outer dimensions of said pole piece,
    said side magnet positioned about the outer periphery of said pole piece; and
    means for adjusting the magnetic flux created by said magnet arrangement, said adjusting means including at least a first cavity formed in said pole piece,
    a first shim positioned within said first cavity, and
    means for positioning said first steel shim at selected orientations and positions within said first cavity,
    said first magnet arrangement positioned within said housing proximate said first open end with said first magnet arrangement side magnet contacting said housing wall;
    a second permanent magnet arrangement comprising a second main magnet formed as a right, cylindrical solid having a central axis, an outer wall and first and second opposed faces perpendicular to said second main magnet axis;
    a second pole piece formed from ferromagnetic material,
    said second pole piece having a central axis and first and second opposed pole piece faces perpendicular to said pole piece axis,
    the first of said pole piece faces being positioned at and coextensive with said second main magnet first face;
    a second side magnet,
    said second side magnet having an inner opening sized and shaped to match the outer dimensions of said second pole piece,
    said second side magnet positioned about the outer periphery of said second pole piece; and
    means for adjusting the magnetic flux created by said second magnet arrangement, said second adjusting means including at least a first cavity formed in said second pole piece,
    a first shim positioned within said first cavity, and
    means for positioning said first shim at selected orientations and positions within said first cavity,
    said second magnet arrangement positioned within said housing proximate said second open end with said second magnet arrangement side magnet contacting said housing wall;
    said second magnet arrangement positioned within said housing proximate said second open end with said second side magnet contacting said housing wall;
    said first and second arrangements spaced apart one from another with said first arrangement second pole piece face facing said second arrangement second pole piece face;
    said first and second arrangements and said housing wall defining therebetween an air gap; and
    an access port formed in said housing wall allowing said tissue to be positioned within said air gap.

2. The apparatus as recited in claim 1 wherein said apparatus produces a magnetic field of about 1.0 tesla and said apparatus weighs about 250 kg.

3. The apparatus as recited in claim 1 wherein said housing is about 60 cm. in diameter.

4. The apparatus as recited in claim 1 wherein said first and second magnet arrangements are sufficiently adjustable to provide a magnetic field of uniform field strength and direction across said air gap.

5. The apparatus as recited in claim 4 wherein said first and second magnet arrangements are sufficiently adjustable to form a diagnostic zone located in said air gap and between said first and second magnet arrangements, said diagnostic zone defined by that portion of said magnetic field found to be the most uniform in field strength and direction.

6. The apparatus as recited in claim 1 further comprising first and second end caps, said first end cap sized and shaped to close off said first open end of said housing, and said second end cap sized and shaped to close off the second open end of said housing.

7. The apparatus as recited in claim 6 wherein said first end cap contacts said second face of said first main magnet and said second end cap contacts said second face of said second main magnet.

8. The apparatus as recited in claim 1 wherein said apparatus further includes a second arrangement of shims to adjust said magnetic field,
said second shim arrangement comprising at least one circumferential groove formed on said housing proximate one said magnet arrangement,
said groove being coaxial with said main magnet axis;
at least one steel shim positioned within said groove; and
means for positioning said steel shim at selected orientations and positions within said groove.

9. The apparatus as recited in claim 8 wherein one said second shim arrangement is formed on said housing proximate each said magnet arrangement.

10. The apparatus as recited in claim 1 wherein said apparatus further comprises an array of RF coils disposed within said air gap,
selected of said coils acting as transmitters and selected of said coils acting as receivers to pulse and detect electromagnetic signals across said magnetic field.

11. The apparatus as recited in claim 10 wherein said apparatus further comprises means to detect and analyze said signals and to select that combination of coils to pulse and detect said signals that produces the most satisfactory MRI image of said tissue.

12. A permanent magnet arrangement for use in apparatus performing MRI analysis of living tissue, said arrangement comprising:
a main magnet formed as a right, cylindrical solid having a central axis, an outer wall and first and second opposed faces perpendicular to said main magnet axis;
a pole piece formed from ferromagnetic material,
said pole piece having a central axis and first and second opposed pole piece faces perpendicular to said pole piece axis,
the first of said pole piece faces being positioned at and coextensive with said first main magnet face;
a side magnet,
said side magnet having an inner opening sized and shaped to match the outer dimensions of said pole piece,
said side magnet positioned about the outer periphery of said pole piece; and
means for adjusting the magnetic flux created by said magnet arrangement, said adjusting means including first, second and third cavities formed in said pole piece,
said first cavity formed in the shape of a right circular cylinder,
each of said second and third cavities formed in the shape of a circular channel,
said first, second and third cavities being concentric one with the other and being centered with respect to said pole piece axis;
a first shim dimensioned to fit within and positioned within said first cavity,
a second shim dimensioned to fit within and positioned within said first cavity, and
a third shim dimensioned to fit within and positioned within said third cavity; and
means for adjusting each said shim with respect to said pole piece, said adjusting means including a plurality of bolts rotatably journaled to each said shim,
each said bolt being individually axially adjustable with respect to said pole piece whereby each said shim may be positioned in a direction in to or outward from each said cavity and whereby each said shim may be positioned at a tilt with respect to said pole piece axis.

13. The apparatus as recited in claim 12 wherein said second and third cavities are rectangular in cross-section and said second and third shims are formed as toroidal rings having rectangular cross-sections.

14. The apparatus as recited in claim 12 wherein said first, second and third cavities are formed in said pole piece first face and said adjusting bolts extend from said pole piece second pole piece face to said shims.

15. The apparatus as recited in claim 12 wherein said first, second and third cavities are formed in said pole piece second face and said adjusting bolts extend from said pole piece second pole piece face to said shims.

* * * * *